(12) United States Patent
Suzuki (10) Patent No.: US 9,155,586 B2
(45) Date of Patent: Oct. 13, 2015

(54) TREATMENT TOOL FOR ENDOSCOPE

(75) Inventor: Keita Suzuki, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 436 days.

(21) Appl. No.: 13/618,325

(22) Filed: Sep. 14, 2012

(65) Prior Publication Data

US 2013/0012986 A1    Jan. 10, 2013

Related U.S. Application Data (63) Continuation of application No. PCT/JP2012/050246, filed on Jan. 10, 2012.

(30) Foreign Application Priority Data

Feb. 23, 2011 (JP) ................................. 2011-037222

(51) Int. Cl.
*A61B 17/00* (2006.01)
*A61B 18/14* (2006.01)
*A61B 19/00* (2006.01)
(Continued)

(52) U.S. Cl.
CPC .............. *A61B 18/1445* (2013.01); *A61B 17/29* (2013.01); *A61B 19/30* (2013.01); *A61B 2017/2946* (2013.01); *A61B 2018/0091* (2013.01)

(58) Field of Classification Search
CPC ............... A61B 2017/2912; A61B 2017/2902; A61B 18/1445; A61B 17/29; A61B 19/30; A61B 2018/0091; A61B 2017/2946
USPC ................................................... 606/205–208
See application file for complete search history.

(56) References Cited

U.S. PATENT DOCUMENTS 4,043,323 A * 8/1977 Komiya ......................... 600/104
4,122,856 A * 10/1978 Mosior et al. .................. 606/170
4,441,563 A * 4/1984 Walton, II ..................... 173/213
(Continued)

FOREIGN PATENT DOCUMENTS

EP    0 538 984 A2    4/1993
EP    1 832 222 A2    9/2007
(Continued)

OTHER PUBLICATIONS

International Search Report issued in International Application No. PCT/JP2012/050246 dated Feb. 14, 2012 (w/translation).
(Continued)

*Primary Examiner* — Amy R Weisberg
(74) *Attorney, Agent, or Firm* — Oliff PLC (57) ABSTRACT

A treatment tool for endoscope includes a pair of forceps members supported so as to be relatively movable by a rotation shaft, an operation section for performing opening/close operations of the forceps members, and an operation wire for connecting the forceps members to the operation section, wherein the operation section has an operation section main body, a first operation member to which the operation wire is connected and which is slideably attached to the operation section main body, a second operation member which is slideably attached to the first operation member, a force adjustment member which is attached to the second operation member and is compressed by the second operation member is slid to the first operation member.

6 Claims, 10 Drawing Sheets

(51) Int. Cl.
*A61B 17/29* (2006.01)
*A61B 18/00* (2006.01)

(56) References Cited

U.S. PATENT DOCUMENTS

| | | | | |
|---|---|---|---|---|
| 4,763,668 A | * | 8/1988 | Macek et al. | 600/564 |
| 4,815,476 A | * | 3/1989 | Clossick | 600/564 |
| 4,945,920 A | * | 8/1990 | Clossick | 600/564 |
| 5,094,247 A | * | 3/1992 | Hernandez et al. | 600/564 |
| 5,100,430 A | * | 3/1992 | Avellanet et al. | 606/205 |
| 5,228,451 A | * | 7/1993 | Bales et al. | 600/564 |
| 5,242,458 A | * | 9/1993 | Bendel et al. | 606/147 |
| 5,250,056 A | | 10/1993 | Hasson | |
| 5,308,357 A | * | 5/1994 | Lichtman | 606/205 |
| 5,415,177 A | * | 5/1995 | Zadini et al. | 600/585 |
| 5,419,339 A | * | 5/1995 | Palmer | 600/564 |
| 5,439,478 A | * | 8/1995 | Palmer | 606/205 |
| 5,454,378 A | * | 10/1995 | Palmer et al. | 600/564 |
| 5,628,757 A | * | 5/1997 | Hasson | 606/148 |
| 5,645,556 A | | 7/1997 | Yoon | |
| 5,683,413 A | * | 11/1997 | Miyagi | 606/205 |
| 5,706,824 A | * | 1/1998 | Whittier | 600/564 |
| 5,810,876 A | * | 9/1998 | Kelleher | 606/205 |
| 5,993,474 A | * | 11/1999 | Ouchi | 606/206 |
| 6,027,522 A | * | 2/2000 | Palmer | 606/205 |
| 6,149,607 A | * | 11/2000 | Simpson et al. | 600/567 |
| 6,206,872 B1 | * | 3/2001 | Lafond et al. | 606/1 |
| 6,210,398 B1 | * | 4/2001 | Ouchi | 606/1 |
| 6,264,617 B1 | * | 7/2001 | Bales et al. | 600/564 |
| 6,299,630 B1 | * | 10/2001 | Yamamoto | 606/205 |
| 6,569,105 B1 | * | 5/2003 | Kortenbach et al. | 600/562 |
| 6,689,122 B2 | * | 2/2004 | Yamamoto | 606/1 |
| 2001/0021859 A1 | * | 9/2001 | Kawai et al. | 606/205 |
| 2005/0006432 A1 | | 1/2005 | Racenet et al. | |
| 2005/0125026 A1 | * | 6/2005 | Prestel et al. | 606/205 |
| 2005/0240218 A1 | * | 10/2005 | Freed et al. | 606/205 |
| 2010/0191260 A1 | * | 7/2010 | Mohajer | 606/144 |
| 2010/0274278 A1 | * | 10/2010 | Fleenor et al. | 606/206 |
| 2011/0196419 A1 | * | 8/2011 | Cooper | 606/206 |
| 2012/0109185 A1 | * | 5/2012 | Fleenor et al. | 606/205 |
| 2013/0012986 A1 | * | 1/2013 | Suzuki | 606/208 |
| 2013/0046338 A1 | * | 2/2013 | Suzuki et al. | 606/205 |
| 2013/0289616 A1 | * | 10/2013 | Suzuki et al. | 606/205 |
| 2013/0324803 A1 | * | 12/2013 | Mohajer | 600/249 |
| 2015/0005813 A1 | * | 1/2015 | Maslanka et al. | 606/206 |

FOREIGN PATENT DOCUMENTS

| | | |
|---|---|---|
| JP | A-10-290803 | 11/1998 |
| JP | A-2004-8367 | 1/2004 |
| JP | A-2004-73634 | 3/2004 |
| JP | A-2007-524451 | 8/2007 |
| WO | WO 2004/112618 A2 | 12/2004 |

OTHER PUBLICATIONS

Extended European Search Report issued in European Application No. 12750105.4 dated Oct. 30, 2012.

\* cited by examiner

TREATMENT TOOL FOR ENDOSCOPE

The present application is a Continuation of International Patent Application No. PCT/JP2012/050246, filed Jan. 10, 2012, claiming priority on Japanese Patent Application No. 2011-37222 filed in Japan on Feb. 23, 2011, the the contents of said Japanese Patent Application and said PCT Application being incorporated herein.

BACKGROUND OF THE INVENTION

1. Field of the Invention

The present invention relates to a treatment tool for endoscope that is used by being endoscopically inserted into a body cavity.

2. Description of Related Art

In the related art, a forceps having a pair of forceps members supported so as to be relatively rotatable to each other via a rotation shaft is known as a treatment tool for endoscope (hereinafter, simply referred to as a "treatment tool") which has a flexible sheath and is used by being endoscopically inserted into a body cavity.

The pair of forceps members is connected to an operation section of a hand side by an operation wire. The pair of forceps members has a configuration that is relatively rotated around the rotation shaft, and is opened and closed, by the operation wire being advanced and retreated in an axial direction via the operation section.

In such a forceps, if the operation wire is continuously retreated even after the pair of forceps members is closed, a large amount of force is acted by the forceps members. For this reason, when the operation wire is further retreated in a state in which a tissue or the like is grasped by the forceps members, the force grasping the tissue becomes excessively large, and thus a burden is applied to the grasped tissue.

Japanese Unexamined Patent Application, First Publication No. H10-290803 suggests a treatment tool including display means which detects and displays an amount of force acted on a treatment section such as the forceps member accompanied by the operation of an operation slider for advancing and retreating the operation wire advanced and retreat using an amount of deflection of an elastic body. An operator is able to adjust the amount of force acted on the treatment section by detecting the amount of force acted on the treatment section using the display means and adjusting an amount of operation of the operation slider.

Most of the treatment tools are inserted through a channel of the endoscope, and are inserted into a body cavity. However, the endoscope can easily move erratically within a body, and in that case, the sheath inserted through the channel also expands and contracts along with the erratic movement of the endoscope. When the sheath expands and contracts, a relationship between the amount of operation of the operation section and the amount of force acted on the treatment section is changed.

SUMMARY OF THE INVENTION

An endoscope treatment tool according to a first aspect of the present invention includes a pair of forceps members supported so as to be relatively movable by a rotation shaft, an operation section for performing open and close operations of the pair of forceps members, and an operation wire for connecting the pair of forceps members to the operation section. Moreover, the operation section has an operation section main body, a first operation member to which the operation wire is connected and which is slideably attached to the operation section main body, a second operation member which is slideably attached to the first operation member, a force adjustment member which is attached to the second operation member and is compressed by the second operation member being slid to the first operation member, and a force-retaining member that is arranged so as to be capable of approaching and separating from the operation section main body. Moreover, the operation section is configured so that, when the force adjustment member is compressed by a predetermined amount, the force-retaining member is moved so as to approach the operation section main body by the second operation member, and the first operation member is fixed to the operation section main body.

In the endoscope treatment tool for endoscope according to a second aspect of the present invention, the first operation member has a through-hole that extends in a direction perpendicular to a sliding direction and exposes a part of the operation section main body. Moreover, the force-retaining member is a pin member arranged in the through-hole.

The endoscope treatment tool for endoscope according to a third aspect of the present invention further includes a control section that controls an amount of compression in an initial state of the force adjustment member.

The endoscope treatment tool for endoscope according to a fourth aspect of the present invention further includes a maximum force control section that controls an amount of force generated in a treatment section in a state in which the first operation member is fixed to the operation section main body.

BRIEF DESCRIPTION OF THE DRAWINGS

FIG. 5 is a diagram that shows an operation when using the operation section of the first embodiment of the present invention.

DETAILED DESCRIPTION OF THE INVENTION

An endoscope treatment tool for endoscope of a first embodiment of the present invention will be described with reference to FIGS. 1 to 6.

Figure 1:
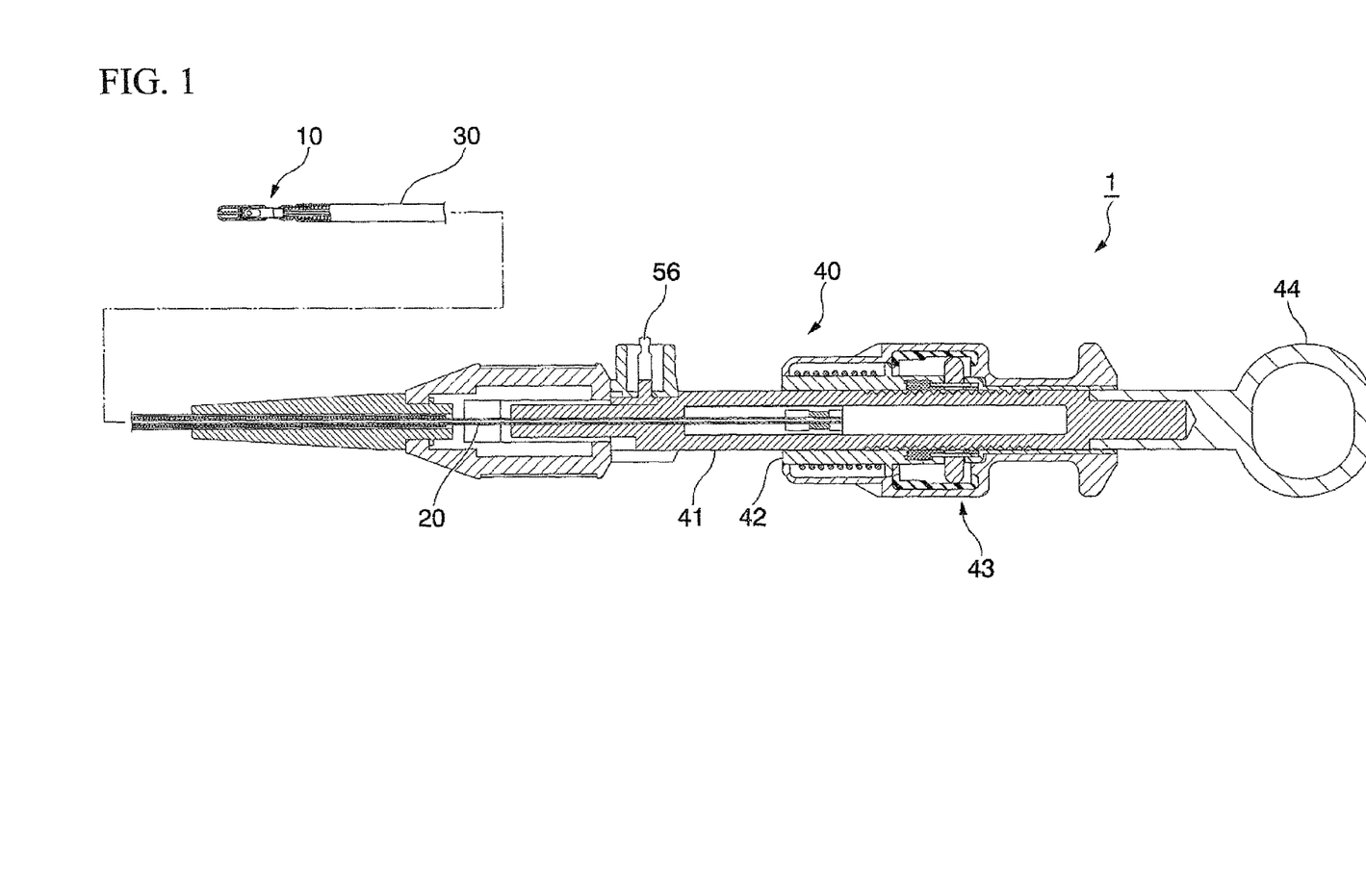
FIG. 1 is an overall diagram that shows an endoscope treatment tool for endoscope of a first embodiment of the present invention in a partial cross-section.

As shown in FIG. 1, a treatment tool 1 of the present embodiment includes a treatment section 10 for treating tissues in a body cavity, an operation section 40 for operating the treatment section 10, an operation wire 20 for connecting the treatment section 10 to the operation section 40, and an elongated insertion section 30 inserted into the body cavity.

Figure 2:
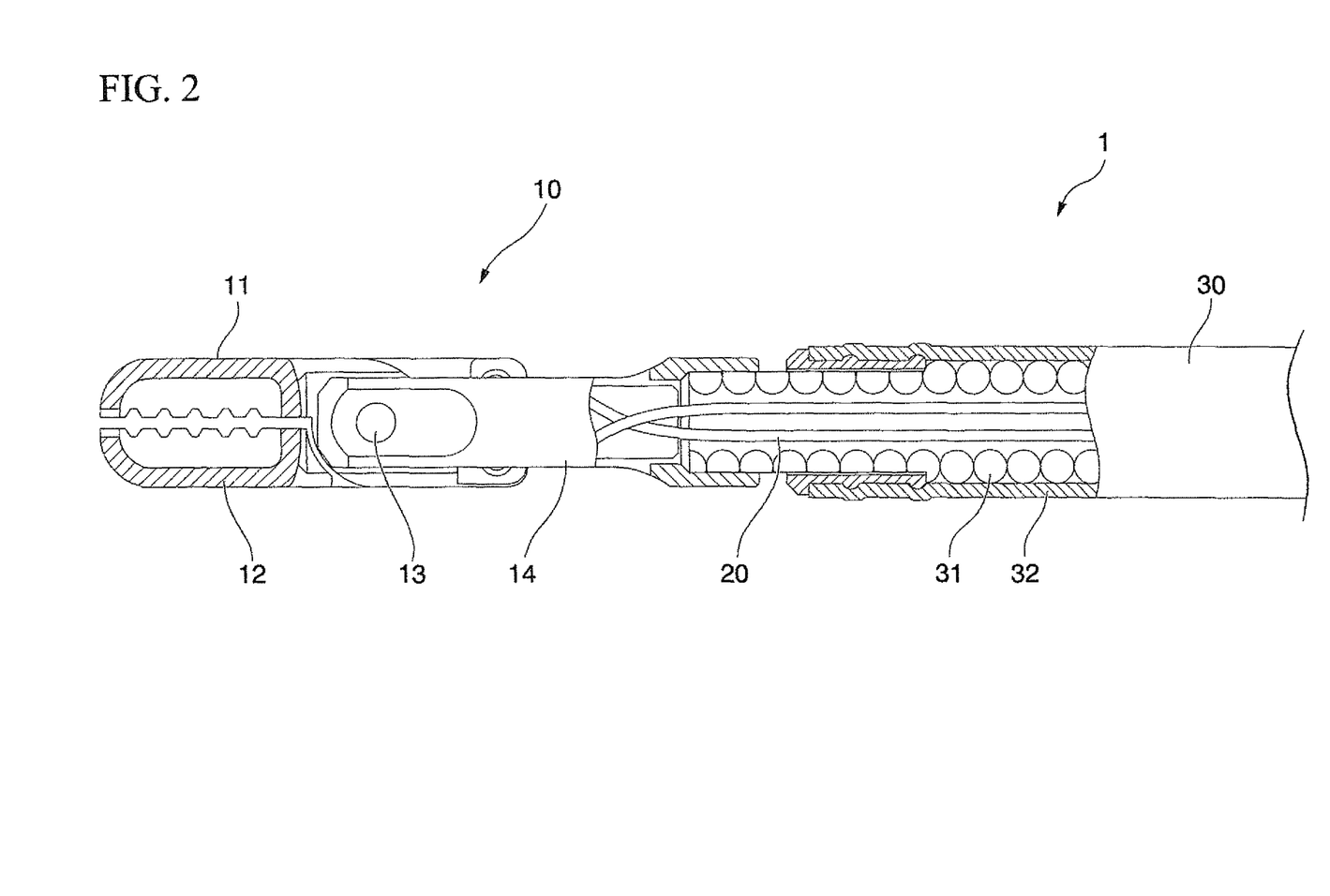
FIG. 2 is an enlarged view that shows a distal end portion of the endoscope treatment tool for endoscope of the first embodiment of the present invention in a partial cross-section.

FIG. 2 is an enlarged view that shows a distal end portion of the treatment tool 1 including the treatment section 10 in a partial cross-section. The treatment section 10 is configured so that a rotation shaft 13 is supported on a cover member 14 and a pair of forceps members including a first forceps member 11 and a second forceps member 12 is relatively and rotatably connected to and supported by the rotation shaft 13. The operation wire 20 is connected to a proximal end side from the rotation shaft 13 of the respective forceps members 11 and 12. The operation wire 20 is connected to the operation section 40 through inside of the insertion section 30.

The insertion section 30 is formed in a long cylinder shape through which the operation wire 20 is inserted, and has a coil sheath 31 and an insulating tube sheath 32 covering the outside of the coil sheath 31. The cover member 14 is fixed to a distal end of the insertion section 30. Moreover, the rotation shaft 13 is supported on the cover member 14 so as not to be moved relative to the cover member 14. A proximal end side of the insertion section 30 is attached to the operation section 40.

Figure 3:
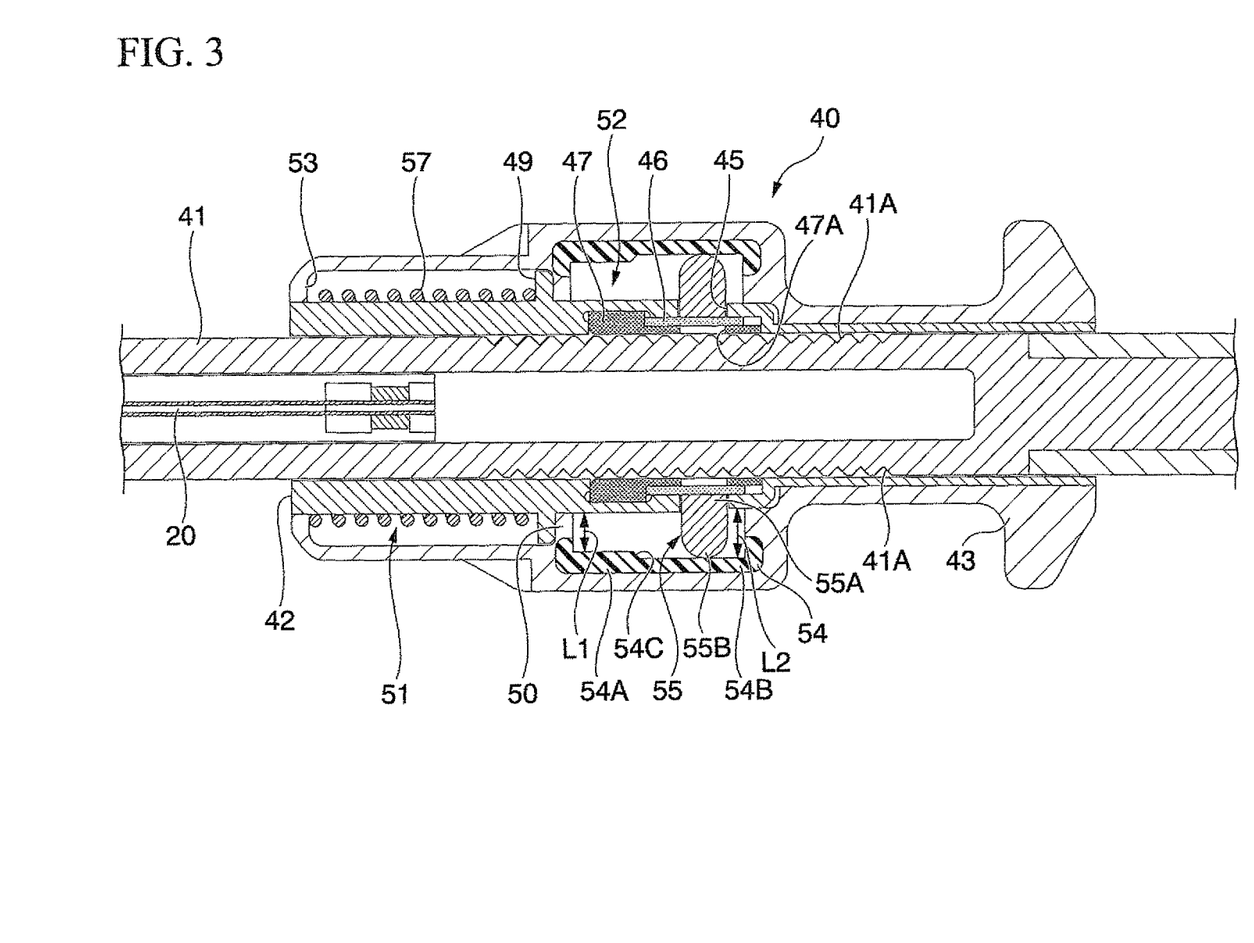
FIG. 3 is an enlarged cross-sectional view that shows an operation section of the endoscope treatment tool for endoscope of the first embodiment of the present invention.

FIG. 3 is an enlarged cross-sectional view of the operation section 40. The operation section 40 includes an operation section main body 41 through which the operation wire 20 is inserted, a first slider (a first operation member) 42 slideably attached to the operation section main body 41, and a second slider (a second operation member) 43 slideably attached to the first slider 42.

The operation section main body 41 is formed of a resin or the like in a substantially cylindrical shape, and the interior thereof has a space through which the operation wire 20 is inserted. A partial region of an outer circumferential surface of the operation section main body 41 in a longitudinal direction is formed with V grooves 41A extending in a circumferential direction. On a proximal end side of the operation section main body 41, a finger engaging handle 44 (see FIG. 1) is provided.

The first slider 42 is formed of a resin or the like in a substantially cylindrical shape. An inner diameter of the first slider 42 is slightly greater than an outer diameter of the operation section main body 41. Circular through-holes 45 communicating with an inner cavity are formed in two places of the outer circumference of the first slider 42. In the present embodiment, although two through-holes 45 are formed at a position facing each other with an axis of the first slider 42 interposed therebetween, the placement need not necessarily be as described.

A part of the inserted operation section main body 41 is exposed to the respective through-holes 45. However, a flexible tube 46 is arranged on an inner surface of the first slider 42 of the position at which the through-holes 45 are opened. The respective through-holes 45 are caulked by the tube 46. The tube 46 is fixed to the first slider 42 by a substantially cylindrical pressing member 47. The pressing member 47 is formed with a through-hole 47A at a position corresponding to the through-hole 45. The pressing member 47 is attached to the first slider 42 so that a phase of the through-hole 45 substantially coincides with that of the through-hole 47A of the pressing member 47 in a circumferential direction thereof. Thus, the tube 46 is able to be deformed so as to protrude to the inner cavity of the first slider 42.

On the inner surface of the first slider 42, in a part to which the tube 46 and the pressing member 47 are attached, concave sections corresponding to the thickness of each member are formed. The inner diameter of the first slider 42 is substantially constant due to the attachment of the tube 46 and the pressing member 47.

In addition, on an outer circumferential surface of the first slider 42, on a distal end side from the part to which the tube 46 and the pressing member 47 are attached, a flange 49 protruding to the outside in a diameter direction is provided.

The second slider 43 is formed of a resin or the like in a cylindrical shape, and the operation section main body 41 and the first slider 42 are inserted into an inner cavity thereof. The inner cavity of the second slider 43 is divided into a first inner cavity 51 of a distal end side and a second inner cavity 52 of a proximal end side by a wall section 50 protruding to the inner cavity over a circumferential direction.

The first inner cavity 51 is a substantially circular cylinder-shaped space in which the flange 49 of the first slider 42 is capable of being moved. An inner diameter of an opening of a distal end of the second slider 43 is set to be slightly greater than an outer diameter of the first slider 42, and a distal end wall section 53 is formed on the distal end side of the first inner cavity 51.

A coil spring 57 (a force adjustment member) is accommodated in the first inner cavity 51. A part of the distal end side of the first slider 42 from the flange 49 is inserted into the coil spring 57. That is, the coil spring 57 is arranged between the flange 49 and the distal end wall section 53 in the first inner cavity 51 and is compressed when causing the second slider 43 to slide to the proximal end side with respect to the first slider 42. In a state in which the coil spring 57 is not compressed, the coil spring 57 presses the flange 49 of the first slider 42 so as to come into contact with the wall section 50 of the second slider 43. For this reason, the first slider 42 and the second slider 43 are integrated and slide with respect to the operation section main body 41.

The second inner cavity 52 is a substantially circular cylinder-shaped space having a diameter greater than that of the first inner cavity 51, and the through-hole 45 of the first slider 42 is opened. A pattern member 54 for changing the diameter of the second inner cavity 52 is arranged on an inner surface of the second slider 43 located on the second inner cavity 52.

The pattern member 54 is a substantially cylindrical member, and has a first region 54A with a thick thickness and relatively small inner diameter and a second region 54B with a thin thickness and relatively large inner diameter. A slope surface-shaped third region 54C having a gradually changing inner surface is formed between the first region 54A and the second region 54B.

The pattern member 54 is attached to the second slider 43 so that the first region 54A is located at the distal end side. In an initial state before operating the treatment tool 1 shown in FIG. 3, the through-hole 45 is located within the range of the second region 54B of the pattern member 54.

Pin members (force-retaining members) 55 are arranged by insertion into the respective through-holes 45 of the first slider 42 so as to protrude into the second inner cavity 52. The pin members 55 is capable of advancing and retreating in the through-hole 45 so as to approach and separate from the operation section main body 41. A first end section 55A inserted into the through-hole 45 is in contact with the tube 46 caulking the through-hole 45. A second end section 55B of the pin member 55 protruding into the second inner cavity 52 is formed with a curved surface. A protruding length of the pin member 55 to the second inner cavity 52 is set to be longer than a distance L1 between the inner surface of the pattern member 54 and the first slider 42 in the first region 54A and shorter than a distance L2 between the inner surface of the pattern member 54 and the first slider 42 in the second region 54B.

A proximal end section of the operation wire 20 is fixed to the first slider 42. By causing the first slider 42 to slide relative to the operation section main body 41, the operation wire 20 advances and retreats, and the pair of forceps members 11 and 12 of the treatment section 10 are capable of being opened and closed.

Furthermore, as shown in FIG. 1, the operation section 40 is provided with a plug 56 for supplying electricity to the treatment section 10. When the plug 56 is connected to a high-frequency power source (not shown), a high-frequency electric current can be supplied to the treatment section 10 via the operation wire 20.

An operation of the treatment tool 1 configured as above during use will be described.

Firstly, an endoscope (not shown) is inserted into a body of a patient, and a distal end of the endoscope is caused to advance up to the vicinity of an in-body cavity tissue to be treated (a target tissue).

A user causes the second slider 43 to slide in the direction of the proximal end side of the operation section main body 41 (hereinafter, the operation in this direction is referred to as "retreating"). Then, since the first slider 42 slide with the second slider 43 in the retreating direction, the pair of forceps members 11 and 12 is in a closed state. The treatment section 10 and the insertion section 30 are inserted into the forceps channel of the endoscope in this state. Moreover, the treatment section 10 is projected from the distal end of the forceps channel.

The user operates the operation section 40 while observing the target tissue with the endoscope, and performs the treatment on the target tissue using the treatment section 10.

When opening the pair of forceps members 11 and 12, the second slider 43 is caused to slide in the direction of the distal end side of the operation section main body 41 (herein, the operation of this direction is referred to as "advancing"). Then, since the first slider 42 slide with the second slider 43 in the advancing direction, the operation wire 20 connected to the first slider 42 advances. As mentioned above, the rotation shaft 13 is supported on the cover member 14 attached to the insertion section 30. For this reason, the first forceps member 11 and the second forceps member 12 are rotated around the rotation shaft 13 fixed to the insertion section 30, and then, the treatment section 10 is opened.

When the first forceps member 11 and the second forceps member 12 are arranged so that the target tissue is located between the first forceps member 11 and the second forceps member 12 and the user causes the second slider 43 to retreat, the target tissue is interposed between and grasped by the first forceps member 11 and the second forceps member 12.

Although the second slider 43 is capable of slightly retreating even after the target tissue is compressed, when the target tissue contracts to some degree, the second slider 43 is capable of no longer retreating. When pulling the second slider 43 so as to retreat in this state, the pulling force is transmitted to the pair of forceps members 11 and 12 via the operation wire 20, and an interposing force by which the target tissue is interposed is increased.

Figure 4:
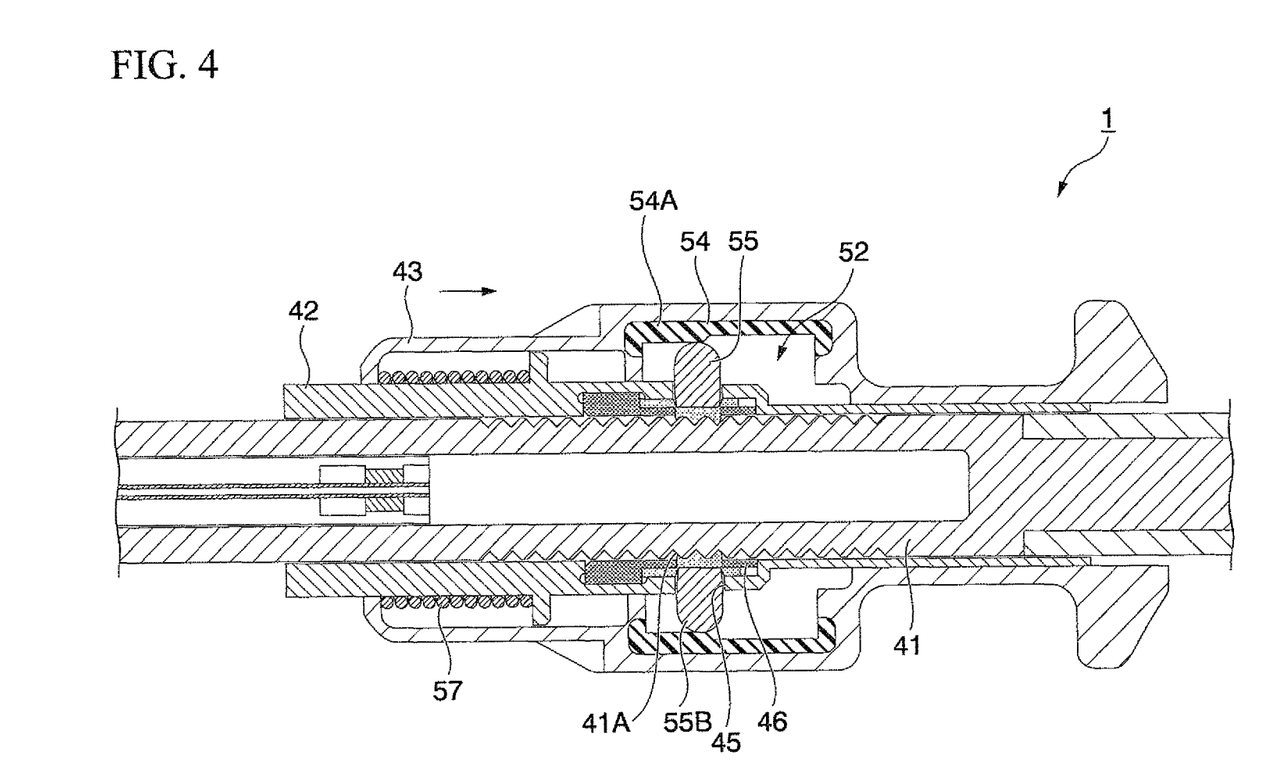
FIG. 4 is a diagram that shows an operation when using the operation section of the first embodiment of the present invention.

When an amount of force pulling the second slider 43 is increased to a magnitude capable of compressing the coil spring 57, as shown in FIG. 4, the second slider 43 retreats relative to the first slider 42 by compressing the coil spring 57.

When the second slider 43 retreats relative to the first slider 42, the pin member 55 is relatively moved so as to advance in the second inner cavity 52, and comes into contact with the first region MA of the pattern member 54. Then, the pin member 55 is pressed to the inner surface of the first region 54A, is pushed into the through-hole 45, and pushes the tube 46 toward the operation section main body 41. The pushed tube 46 protrudes into the inner cavity of the first slider 42, comes into contact with the operation section main body 41, and generates a large frictional force between the operation section main body 41. At this time, a part of the tube 46 enters and is engaged with the V groove 41 formed in the operation section main body 41. Thus, the first slider 42 is held by the frictional force so that it is not capable of substantially sliding with respect to the operation section main body 41, and the amount of force acted on the target tissue from the treatment section 10 is constantly maintained.

When supplying the high-frequency electric current from the plug 56 to the treatment section 10 in the state in which the target tissue is grasped, the grasped target tissue is cauterized.

According to the treatment tool 1 of the present embodiment, when the amount of force pulling on the second slider 43 is a predetermined magnitude, firstly, the coil spring 57 is compressed, and the interlocking between the first slider 42 and the second slider 43 is released. Thus, an excessive force is suppressed from being acted on the target tissue grasped by the treatment section 10.

In addition, when the coil spring 57 is compressed by a predetermined amount, the pin member 55 is moved so as to approach the operation section main body 41 from a state separated from the operation section main body 41, by the first region 54A of the pattern member 54 attached to the second slider 43. Thus, the first slider 42 connected to the operation wire 20 is fixed to the operation section main body 41, and the force acted on the grasped target tissue is constantly maintained.

Accordingly, by performing only the operation as in the treatment tool of the related art in which the slider is pulled so as to retreat, the acted force can be easily maintained in a fixed magnitude while preventing excessive force from being acted on the grasped target tissue. As a consequence, it is possible to more safely perform the treatment on the target tissue with an easier operation.

Furthermore, the first slider 42 is fixed to the operation section main body 41 based on the amount of force acted on the slider but not the amount of movement of the slider. For this reason, even if the initial position of the slider is changed before the operation due to the fact that the insertion section 30 moves erratically in the forceps channel of the endoscope, the magnitude of the maximum force acted on the treatment section 10 is not changed. Thus, the maximum force of the treatment section can be set at a predetermined magnitude without being influenced by the use environment.

Furthermore, since the second end section 55B of the pin member 55 is formed in a shape having the curved surface, the pin member 55 is capable of being smoothly and relatively moved toward the first region 54A in the second inner cavity 52 via the third region 54C. Thus, the effect mentioned above can be obtained without greatly changing a feeling of operation of the user.

The timing in which the interlocking between the first slider 42 and the second slider 43 is released which is capable of being suitably adjusted, for example, by replacing the coil spring with a member of a different spring constant. Furthermore, the timing in which the first slider 42 is fixed to the operation section main body 41 which is capable of being suitably adjusted by changing an inner surface shape of the pattern member 54, for example, lengths of the first region 54A and the second region 54B or the like.

In the present embodiment, an example in which the force-retaining member is the pin member 55, and the pin member 55 presses the tube 46 and causing the tube 46 to come into contact with the operation section main body 41 so that the first slider 42 to the operation section main body 41 has been described. However, the configuration of the force-retaining member is not limited thereto.

Figure 5:
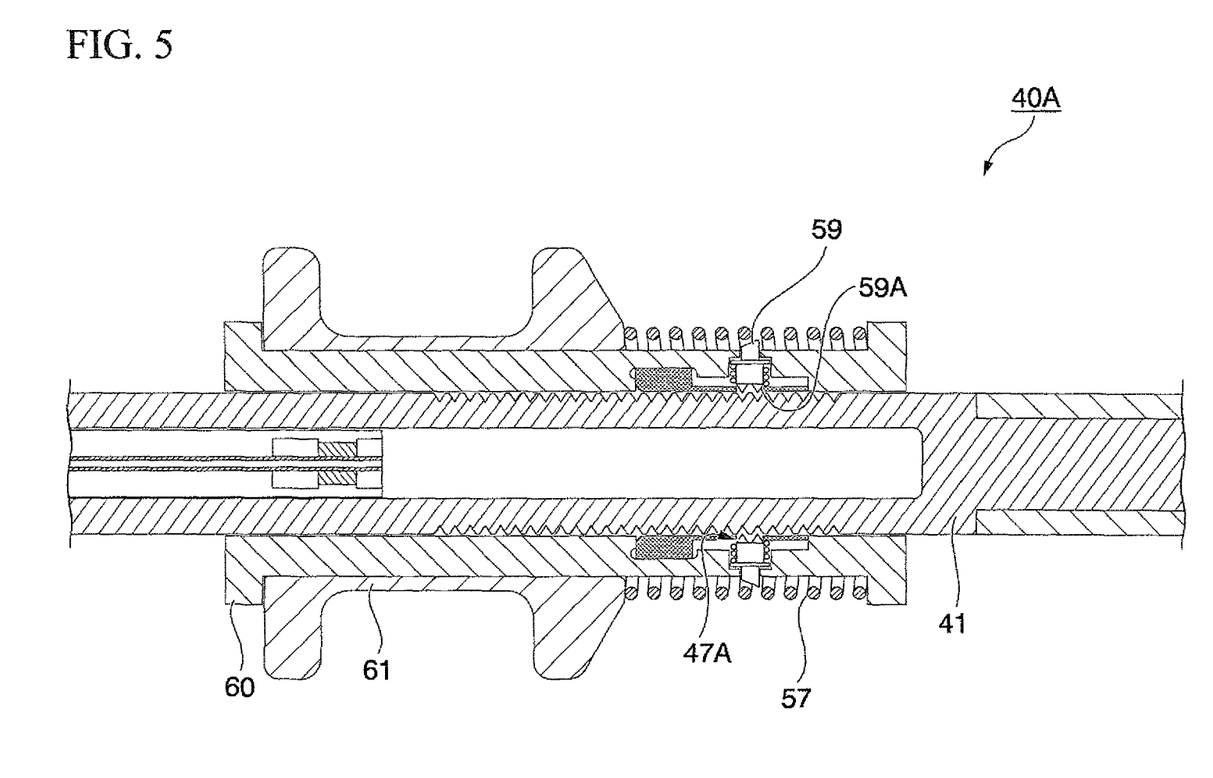
FIG. 5 is a diagram that shows an operation section of a modified example of the endoscope treatment tool for endoscope of the first embodiment of the present invention.
Figure 6:
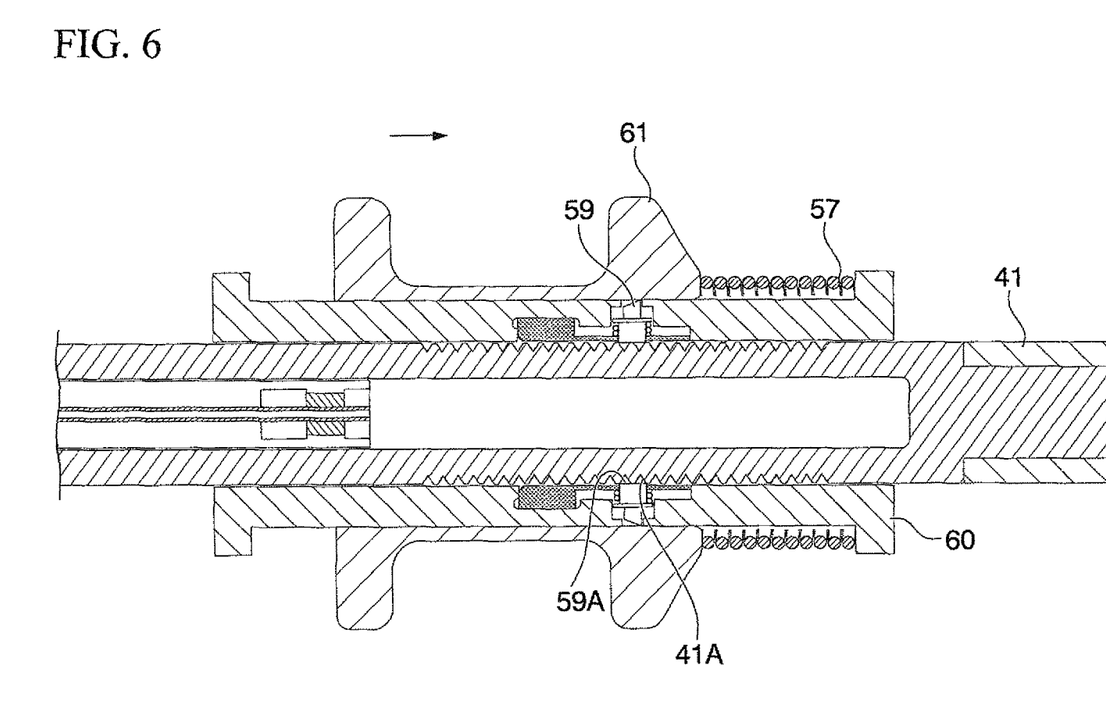

For example, as in an operation section 40A of a modified example shown in FIG. 5, a pin member 59 having an engagement claw 59A in a first end section thereof as the force-retaining member may be arranged in the through-hole 47A of the pressing member 47. In the operation section 40A, the pin member 59 is biased so as to protrude to the outer circumferential surface of a first slider 60 by a biasing member such as a spring. When a second slider 61 retreats relative to the first slider 60 by a predetermined amount while compressing the coil spring 57, as shown in FIG. 6, the second slider 61 presses the pin member 59. Then, the pin member 59 is moved so as to approach the operation section main body 41, the engagement claw 59A is engaged with the V groove 41A, and the first slider 60 is fixed to the operation section main body 41.

Furthermore, as a mechanism for fixing the first slider to the operation section main body, for example, it is possible to use various known mechanisms such as an aspect in which the pin member enters a hole formed in the operation section main body and functions as a knock pin.

Next, a second embodiment of the present invention will be described with reference to FIG. 7. A treatment tool 71 of the present embodiment is different from the treatment tool 1 of the first embodiment in that the former further includes a control section for controlling an amount of compression in the initial state of the force adjustment member.

In the description below, configurations common to the treatment tools of each embodiment mentioned above will be denoted by the same reference numerals, and the repeated description will be omitted.

Figure 7:
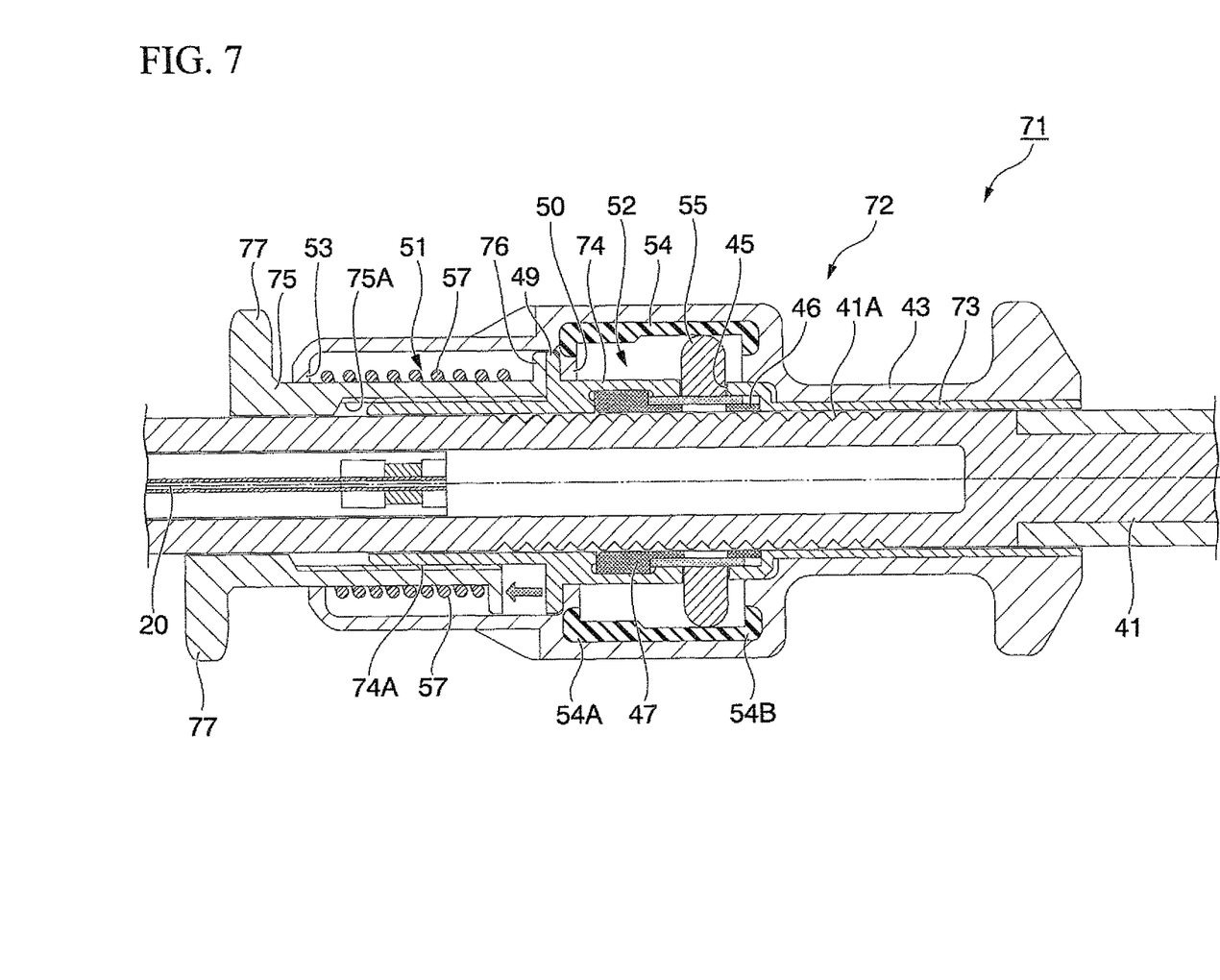
FIG. 7 is an enlarged cross-sectional view that shows an operation section of an endoscope treatment tool for endoscope of a second embodiment of the present invention.

FIG. 7 is a partially enlarged cross-sectional view that shows an operation section 72 of the treatment tool 71. A first slider 73 is constituted by a first member 74 formed with the through-hole 45, and a second member (a control section) 75 screwed with the first member 74.

The second member 75 has an internal thread section 75A. The internal thread section 75A is screwed with an external thread section 74A provided at the distal end side from the flange 49 of the first member 74, and thus the second member 75 is provided integrally with the flange 49. In the first end section of the proximal end side of the part having the internal thread section 75A of the second member 75, an abutment flange 76 is provided. The coil spring 57 is arranged between the distal end wall section 53 and the abutment flange 76 in the first inner cavity 51. In the second member 75, a second end section of an opposite side (a distal end side) of the first end section protrudes to the distal end side from the second slider 43, and a substantially disc-shaped control dial 77 protruding to the outside in the diameter direction is provided.

The method of using the treatment tool 71 is the same as that of the treatment tool 1. In addition, in the treatment tool 71, when changing the screwing length between the first member 74 and the second member 75 by operating the control dial 77 provided in the operation section 72, as shown in the bottom half of FIG. 7, the abutment flange 76 is moved. Thus, it is possible to adjust the amount of compression of the coil spring 57 in the initial state before the operation. Accordingly, the user can perform the treatment in a state in which an operation is easiest by controlling the amount of compression of the coil spring 57 based on the feeling of operation.

In the present embodiment, although an example in which the control section is provided in the first slider has been described, the control section may be provided in the second slider, for example, by allowing the position of the distal end wall section to be controlled by the same configuration.

Next, a third embodiment of the present invention will be described with reference to FIG. 8. A treatment tool 81 of the present invention is different from the treatment tools of each embodiments mentioned above in that the former further includes a maximum force control section which controls the maximum force generated in the treatment section.

Figure 8:
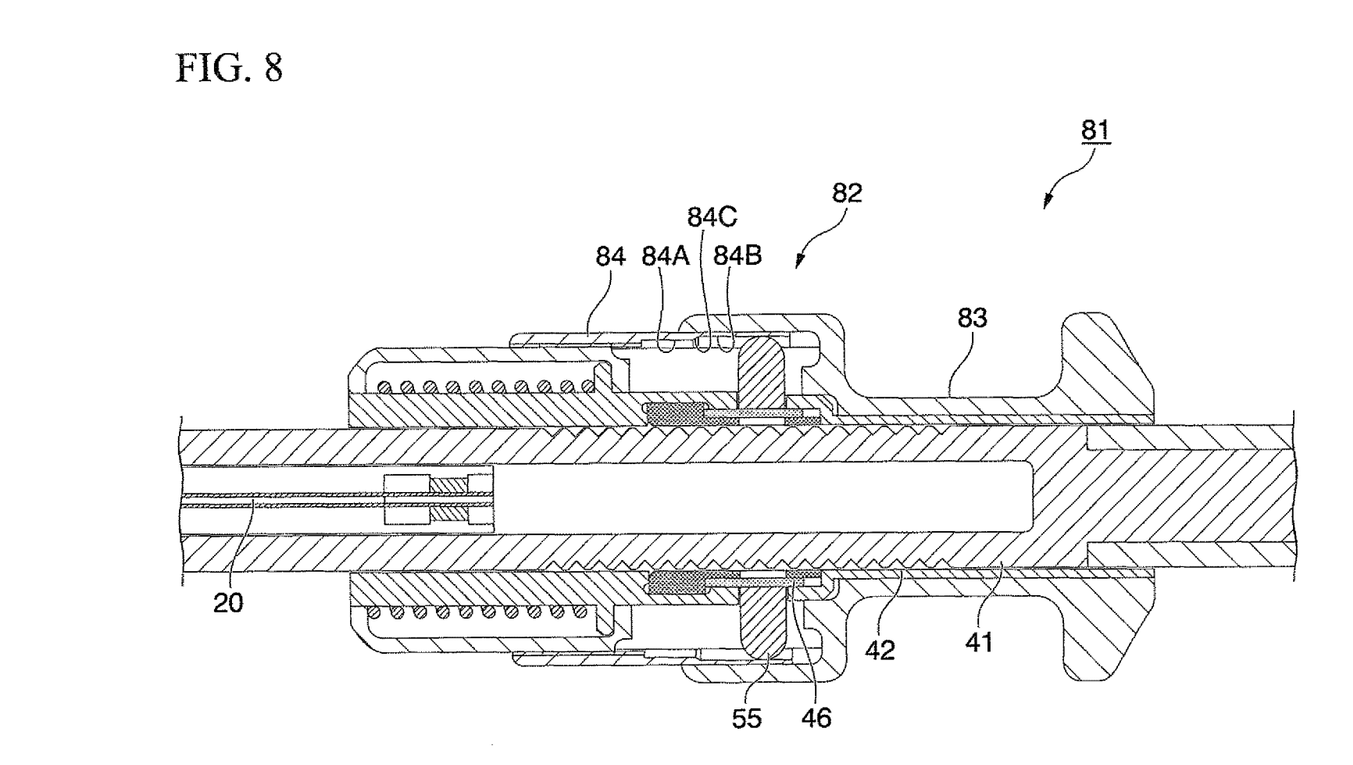
FIG. 8 is an enlarged cross-sectional view that shows an operation section of an endoscope treatment tool for endoscope of a third embodiment of the present invention.

FIG. 8 is a partially enlarged cross-sectional view that shows an operation section 82 of the treatment tool 81. In the operation section 82, a pattern member (a maximum force control section) 84 is screwed with a second slider 83. The pattern member 84 has a first region 84A, a second region 84B and a third region 84C, like the pattern member 54 of the first embodiment and the second embodiment.

In the treatment tool 81, when changing the screwing length of the second slider 83 and the pattern member 84, a positional relationship between the pin member 55 and the pattern member 84 is changed. That is, the timing at which the first region 84A presses the pin member 55 is changed. Thus, by suitably controlling the screwing length, the timing at which the first slider 42 connected with the operation wire 20 is fixed to the operation section main body 41 is capable of being controlled, and the maximum force generated in the treatment section is capable of being controlled to a desired magnitude. As a consequence, procedures or the like can be performed to the maximum force suitable for the type of procedure, target tissues or the like.

Although the respective embodiments of the present invention have been described above, the technical scope of the present invention is not limited to the respective embodiments mentioned above, and it is possible to modify a combination of the components of the respective embodiments, add various modifications to the respective components, or delete them, within the scope that does not depart from the spirit of the present invention.

For example, in the respective embodiments above, although the example in which the maximum force of the treatment section is constantly maintained by fixing the first slider to the operation section main body has been described, the configuration in which the maximum force of the treatment section is constantly maintained is not limited thereto.

Figure 9:
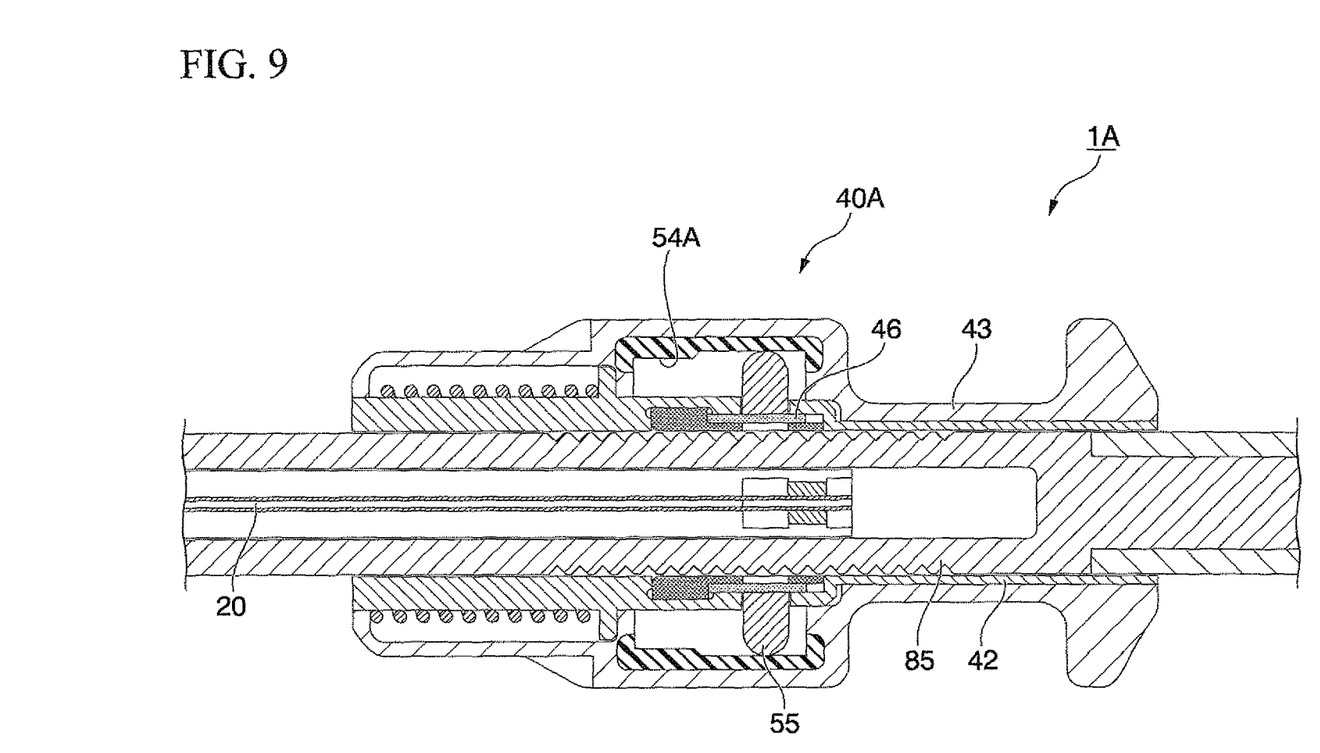
FIG. 9 is an enlarged cross-sectional view that shows an operation section of an endoscope treatment tool for endoscope of a modified example of the present invention.

FIG. 9 is an enlarged cross-sectional view of the operation section 40A in the treatment tool 1A of a modified example of the present invention. In the treatment tool 1A, the proximal end of the operation wire 20 is in an overlapping position with the pin member 55 and the tube 46 in the longitudinal direction of an operation section main body 85. Furthermore, the operation section main body 85 has substantially the same external form as the operation section main body 41 mentioned above. In addition, the operation section main body 85 has rigidity lower than that of the operation section main body 41 and is formed so as to be bent toward the operation wire 20 and deformed by the pressing of the pin member 55.

Figure 10:
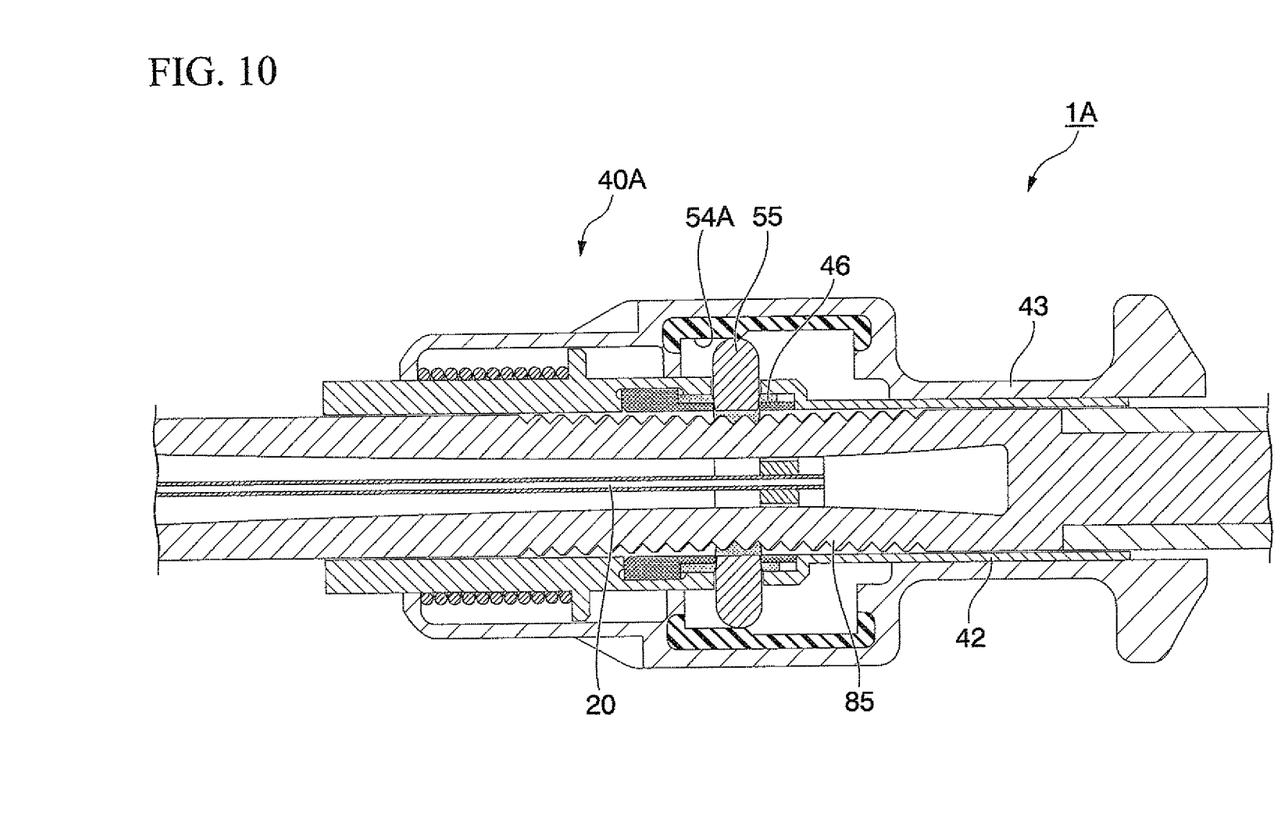
FIG. 10 is a diagram that shows an operation when using the operation section.

In the treatment tool 1A, when the second slider 43 slides relative to the first slider 42 and the pin member 55 is pressed by the first region 54A of the pattern member, as in the first embodiment, the first slider 42 is fixed to the operation section main body 85. In addition, as shown in FIG. 10, the operation section main body 85 pressed by the pin member 55 is bent and deformed, and the proximal end section of the operation wire 20 is interposed, and thus the operation section main body 85 and the operation wire 20 are fixed so as not to be relatively moved. Accordingly, the operation wire 20 is more reliably fixed, and the maximum force in the treatment section is more reliably maintained at a predetermined magnitude.

Furthermore, as another modification, an elastic body may be used as the force adjustment member instead of the coil spring.

Furthermore, the structure of the treatment tool of the present invention can also be applied to a treatment tool which does not provide electricity to the treatment section. In this case, the plug may not be provided.

While preferred embodiments of the invention have been described above, these are not limitative of the invention. Additions, omissions, substitutions, and other modifications can be made without departing from the spirit or scope of the present invention. Accordingly, the invention is not to be considered as being limited by the foregoing description, and is only limited by the scope of the appended claims.

The invention claimed is:

1. A treatment tool for endoscope comprising:
   a pair of forceps members supported so as to be relatively movable by a rotation shaft;
   an operation section configured to perform open and close operations of the pair of forceps members; and
   an operation wire configured to connect the pair of forceps members to the operation section,
   wherein the operation section includes:
      a first operation member which is slidably attached to an operation section main body, and a second operation member which is slidably attached to the first operation member,
      the second operation member is formed in a cylindrical shape, and the operation section main body and the first operation member are inserted into an inner cavity thereof,
      a force-retaining member is arranged in a space formed between the first operating member and the second operating member, the force-retaining member being capable of approaching and separating from the operation section main body,
      a force adjustment member is accommodated in the space formed between the first operating member and the second operating member and is compressed when the second operation member is slid to a proximal end side with respect to the first operation member,
   when an amount of force pulling on the second operation member is less than a predetermined magnitude, the first operation member and the second operation member are interlocked to each other and slide together with respect to the operation section main body, and
   when the amount of force pulling on the second operation member becomes the predetermined magnitude, an interlocking between the first operation member and the second operation member is released and the force-retaining member is forced to approach to the operation section main body by a movement of the second operation member.

2. The treatment tool for endoscope according to claim 1, wherein the first operation member has a through-hole that extends in a direction perpendicular to a sliding direction and exposes a part of the operation section main body, and
   the force-retaining member is a pin member arranged in the through-hole.

3. The treatment tool for endoscope according to claim 1, further comprising:
   a control section that controls an amount of compression in an initial state of the force adjustment member.

4. The treatment tool for endoscope according to claim 1, further comprising:
   a maximum force control section that controls an amount of force generated in a treatment section in a state in which the first operation member is fixed to the operation section main body.

5. The treatment tool for endoscope according to claim 1, wherein the force-retaining member is arranged so as to be capable of approaching and separating from the operation section main body by moving in a direction substantially perpendicular to a direction in which the operation wire extends.

6. The treatment tool for endoscope according to claim 1, wherein the first operation member has a substantially cylindrical shape and extends in a direction parallel with a direction in which the operation wire extends,
   the operation section main body is disposed in an inner space of the first operation member and extends in a direction parallel with the direction in which the operation wire extends, and
   an inner surface of the first operation member is slidably attached to an outer surface of the operation section main body.

* * * * *